United States Patent

Bedeschi et al.

Patent Number: 5,286,861
Date of Patent: Feb. 15, 1994

[54] PROCESS FOR PREPARING URACIL DERIVATIVES

[75] Inventors: Angelo Bedeschi, Milan; Walter Cabri, Rozzano; Ilaria Candiani, Busto Arsizio; Tiziano Martinengo, Carpignano Sesia, all of Italy

[73] Assignee: Farmitalia Carlo Erba S.R.L., Milan, Italy

[21] Appl. No.: 928,507

[22] PCT Filed: Feb. 21, 1991

[86] PCT No.: PCT/EP91/00324
§ 371 Date: Aug. 21, 1992
§ 102(e) Date: Aug. 21, 1992

[87] PCT Pub. No.: WO91/13064
PCT Pub. Date: Sep. 5, 1991

[30] Foreign Application Priority Data

Feb. 22, 1990 [GB] United Kingdom ............. 9004021.3

[51] Int. Cl.$^5$ ................ C07D 239/54; C07D 239/545
[52] U.S. Cl. ..................... 544/309; 544/314; 544/313
[58] Field of Search ............. 544/309, 314, 313

[56] References Cited

U.S. PATENT DOCUMENTS 4,618,604 9/1986 Chu et al. ..................... 514/274

FOREIGN PATENT DOCUMENTS 1250829 9/1967 Fed. Rep. of Germany .

OTHER PUBLICATIONS

Candiani et al, Heterocycles, vol. 24, pp. 875–879 (1992).

*Primary Examiner*—John M. Ford
*Attorney, Agent, or Firm*—Oblon, Spivak, McClelland, Maier & Neustadt

[57] ABSTRACT

The present invention relates to a novel process for preparing uracil derivatives useful as intermediates in the synthesis of uridines having antiviral or antitumor activity or useful as coadjuvants in antiviral therapy, characterized by converting a compound of the formula II into its mesylate derivative of the formula III which is the reduced to give the desired compound of the formula I:

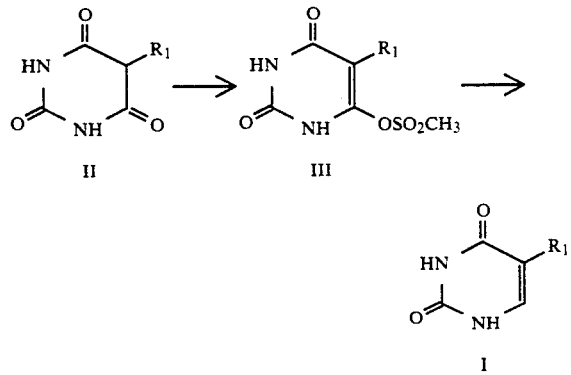

in which $R_1$ is H, halogen, alkyl, aryl or aralkyl.

6 Claims, No Drawings

PROCESS FOR PREPARING URACIL DERIVATIVES

The present invention relates to a novel process for preparing uracil derivatives useful as intermediates in the synthesis uridines having antiviral or antitumor activity or useful as coadjuvants in antiviral therapy. In particular they are, for instance, useful in the synthesis of 5-benzylacyclouridine (BAU) according to the following scheme:

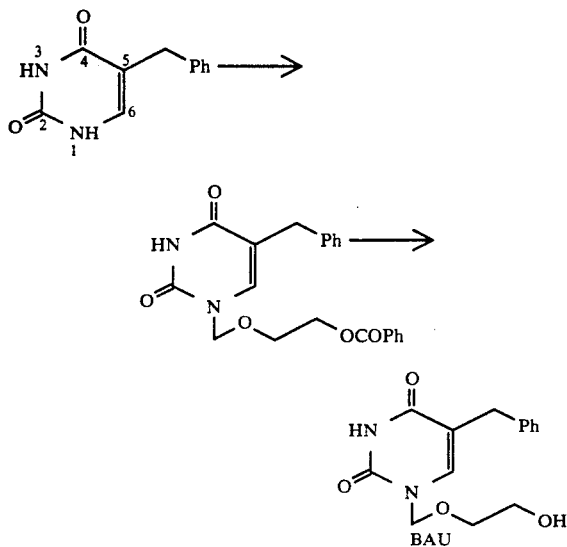

It is known that these uracils may be prepared by cyclisation of a suitable intermediate (see Merck Index, XI Edition, compound 9332 and references cited therein) or by transformation of an uracil derivative, e.g. as described in JP 63 63668. These known methods of preparation require the use of expensive reagents or the use of strong, hazardous base, such as, for instance NaH, which are hardly suitable for industrial preparations.

The present invention provides a simple, low-cost process for the preparation of unsubstituted or 5-halogen, 5-alkyl, aryl or aralkyl substituted uracil derivatives of the formula (I):

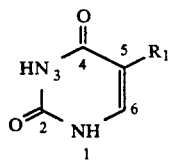

wherein: $R_1$ represents hydrogen or halogen atom, or an optionally substituted alkyl, aryl or aralkyl group, which process comprises converting a compound of the formula II

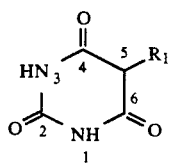

wherein $R_1$ is as defined above, or a salt thereof, into a mesylate derivative of the formula III

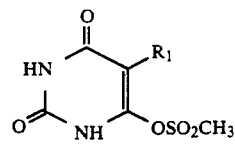

wherein R is as defined above, and then reducing this compound of the formula III to give the desired compound of the formula I.

Indeed DE-1250829 discloses a process in which 6-Cl substituted uracil derivatives, prepared from the corresponding barbituric acid by the use of phosphorus chlorinating agents, are converted to uracil by reduction. But such process is only limited to removal of halogen, particularly chlorine, as is well known in scientific literature (see J. March, Advanced organic Chemistry, 3th ed., pp 389-392). Moreover the preparation of such chlorine derivatives unfortunately requires the use of severe reaction conditions, i.e. the use of the highly corrosive and toxic phosphorous oxyhalides ($POCl_3 + 1\%$ $H_3PO_4$) as solvent at reflux temperature, which greatly limits the applicability of this process to large scale preparations. The process of the present invention takes advantage of the discovery that, due to the inherent symmetry and to the different $pK_A$ of barbituric acid of the formula (II) above defined, the preparation of the monomesylate of formula (III) above defined is possible in one step.

This reaction, in fact, allows the preparation of compounds of formula (III) without affecting the carbonyl group in the 2 position and thus avoiding a protection/-deprotection sequence. Quite surprisingly (see e.g. Advantages in Heterocyclic Chemistry, 38, Recent Progress in Barbituric Acid Chemistry, pp 269-273 and particularly section III.B page 269 and page 271) dimesylated product, N-substituted products, and products arising from scrambling of the mesyl group between the various functionalities were observed only in trace amounts.

Moreover the preparation of the aforementioned mesylate (III) involves the use of very mild reaction conditions, i.e. room temperature in a solvent such as dimethylformamide, and of a reagent-quantity amount of methansulphonyl derivatives.

The present invention also comprises the surprisingly easy reduction of mesylate (III); in fact no precedent is reported in the scientific literature about the reduction of such enol mesylates to the corresponding ene functionality, this kind of reaction being hardly known at all.

This process offers the distinct advantage of the preparation of expensive 5-substituted uracils starting from inexpensive barbituric acid derivatives. This process should be also particularly advantageous from an industrial point of view for the accessibility and low cost of reagents and for the easy and mild reaction conditions. Moreover this methodology avoids the use of hazardous materials allowing greater scale and safer preparation.

In particular, the process of the present invention typically comprises reacting an organic or inorganic salt of as compound of formula (II) as defined above with up to three moles, per mole of the salt of the compound of formula (II), of a suitable methansulphonic derivative, such as, for instance, methansulphonyl chloride or anhydride, in a suitable organic solvent, at a temperature of from −40° C. to 60° C. for a period of from 10 minutes to a day.

Suitable salts include salts with organic bases such as, for instance, alkylamines, mixed arylalkylamines, or with an alkali metal, such as sodium or potassium. The preferred salts are with alkylamines such as, for instance, trialkylamines.

Suitable solvents include dimethylformamide (DMF), tetrahydrofurane, dimethylsulfoxide, methylene chloride, acetonitrile, acetone; the preferred ones being polar, e.g. dimethylformamide, dimethylsulfoxide, tetrahydrofurane or acetonitrile.

The reduction of the compounds of formula (III) as defined above is carried out in a suitable solvent in the presence of a suitable catalyst and of molecular hydrogen or a suitable reducing agent at a temperature of from −20° C. to 60° C. for a period of from 10 minutes to a few, for example 10, hours.

Suitable solvents are alcohols, water, acetic acid, the preferred one being methanol, ethanol, propanol, butanol, water or alcohol-water mixtures.

Suitable catalysts are selected from transition metals, the preferred catalyst being Pd/C, Pd/CaCO$_3$, Pd/BaSO$_4$ or Pt catalyst.

The starting materials are known or may be prepared by known methodologies and as stated above, the defined compounds of the formula I are useful intermediates in the preparation of therapeutically active compounds.

In particular, an object of the present invention is the preparation of compounds of formula I, wherein $R_1$ is preferably:

a) hydrogen or a halogen atom, more preferably hydrogen or a fluorine atom;

b) a $C_1$-$C_4$ alkyl group unsubstituted or substituted by one or more substituents selected from halogen, hydroxy or $C_1$ or $C_2$ alkoxy; more preferably an unsubstituted or halogen-, typically fluorine-, substituted $C_1$-$C_4$, typically $C_1$ or $C_2$ alkyl;

c) a phenyl group optionally substituted by a $C_1$ or $C_2$ alkyl or alkoxy group, more preferably an unsubstituted phenyl ring;

d) a —$(CH_2)_n$Ar group, with n=1 to 4, more preferably with n=1 or 2. Ar is an optionally substituted phenyl group as defined in c) above.

The more preferred embodiment of the present invention is directed to the preparation of the compounds of formula (I) wherein $R_1$ is hydrogen or fluorine atoms, or a $C_1$ or $C_2$ alkyl group unsubstituted or substituted by one or more halogen atom, preferably fluorine, or an unsubstituted $(CH_2)_n$Ar group, wherein n is 1 or 2, preferably 1.

The following Examples illustrate but do not limit the invention.

EXAMPLE 1

5-benzyl-6-methanesulphonyloxy-2,4-(1H,3H)-pyrimidinedione

A solution of methanesulfonyl chloride (1.4 ml) in DMF (20 ml) was dropped into a stirred suspension of the triethylammonium salt of 5-benzyl-2,4,6-(1H,3H)-pyrimidinetrione (g 5) in DMF (210 ml). After an hour most of the solvent was removed in vacuo. The residual suspension was then poured into a ice-water mixture, and the precipitated white solid was collected by filtration, to yield, after drying, the title product, (4 g, 36.2% yield).

MS (EI): 296

UV (Diox.)$\lambda_{max}$(nm):259.6

IR (nujol mull) cm$^{-1}$: 1715, 1670-1650 (broad)

NMR (DMSO-d$_6$)$\delta$(ppm): 11.9 (bs 1H), 11.45 (s 1H), 7.19 (m 5H), 3.70 (s 3H), 3.62 (s 2H).

By analogy the following compounds were prepared:

5-methyl-6-methanesulphonyloxy-2,4-(1H,3H)-pyrimidinedione 5-ethyl-6-methanesulphonyloxy-2,4-(1H,3H)-pyrimidinedione 5-propyl-6-methanesulphonyloxy-2,4-(1H,3H)-pyrimidinedione 5-butyl-6methanesulphonyloxy-2,4-(1H,3H)-pyrimidinedione 5-fluoro-6-methanesulphonyloxy-2,4-(1H,3H)-pyrimidinedione 6-trifluoromethyl-6-methanesulphonyloxy-2,4-(1H,3H)-pyrimidine dione 5-(2-trifluoroethyl)-6-methanesulphonyloxy-2,4-(1H,3H)-pyrimidinedione 6-methanesulphonyloxy-2,4-(1H,3H)-pyrimidinedione NMR (DMSO-d$_6$) $\delta$(ppm): 11.31 (bs, 1H), 5.50 (s, 2H), 3.63 (s, 3H).

EXAMPLE 2

5-benzyl-2,4-(1H,3H)-pyrimidinedione

A solution of 5-benzyl-6-methanesulphonyloxy-2,4-(1H,3H)-pyrimidinedione (3 g) and Et$_3$N (2.1 ml) in MeOH was hydrogenated in the presence of Pd/C 5% (0.3 g) for 3 hr at 35° C. NaOH 5% (2.5 eq) was added and the catalyst filtered off. The solution was acidified to pH 2 with HCl 10%. The precipitated white solid was then collected by filtration, washed with water, ether and dried under vacuum to yield the desired 5-benzyl-2,4-(1H,3H)-pyrimidinedione: 1.635 g, 79.8% yield.

UV (Diox)$\lambda_{max}$(nm):260.4

IR (Nujol mull) cm$^{-1}$:1745, 1690(sh), 1670

NMR (DMSO-d$_6$) $\delta$(ppm): 11.07 (s 1H), 10.69 (bs 1H), 7.23 (m 6H), 3.3 (s 2H).

Analogously starting from the corresponding mesylate the following compounds were prepared:

5-methyl-2,4-(1H,3H)-pyrimidinedione, m.p. >300° C., NMR (DMSO-d$_6$) $\delta$ppm 7.21 (m, 1H) 1.75 (d, 3H)

5-ethyl-2,4-(1H,3H)-pyrimidinedione 5-propyl-2,4-(1H,3H)-pyrimidinedione 5-butyl-2,4-(1H,3H)-pyrimidinedione, m.p. 286-287° C.

EXAMPLE 3

5-benzyl-2,4-(1H,3H)-pyrimidinedione

The reaction was executed as described in Example 2, except that the hydrogenation was carried out at room temperature for 6 hours, yielding the desired 5-benzyl-2,4-(1H,3H)-pyrimidinedione in 70% yield.

Analogously the following compounds were prepared:

5-fluoro-2,4-(1H,3H)-pyrimidinedione, m.p. 283° (dec.). NMR (DMSO-d$_6$/CDCl$_3$) $\delta$(ppm): 11.36 (bs, 1H), 10.60 (bs, 1H), 7.50 (m, 1H)

5-trifluoromethyl-2,4-(1H,3H)-pyrimidinedione 5-(2-trifluoroethyl)-2,4-(1H,3H)-pyrimidinedione

EXAMPLE 4

5-benzyl-2,4-(1H,3H)-pyrimidinedione

The reaction was carried out as described in Example 2 except that the solvent was a water-ethanol 10:1 mixture yielding the title product in 88% yield.

Analogously 2,4-1H,3H)-pyrimidinedione was prepared, m.p. >300° C. NMR (DMSO-$d_6$) δ(ppm): 11.00 (bs, 2H), 7.39 (d, 1H. J=7.4 Hz), 5.45 (d, 1H, J=7.4 Hz)

EXAMPLE 5

5-benzyl-2,4-(1H,3H)-pyrimidinedione

The reaction was carried out as described in Example 4 at room temperature for 10 hours. The title product was obtained in 50% yield.

We claim:

1. A process for preparing a compound of Formula I:

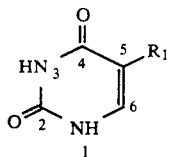

wherein $R_1$ is (i) hydrogen or halogen; (ii) $C_{1-4}$ alkyl, or $C_{1-4}$ alkyl substituted by at least one substituent selected from the group consisting of halogen, hydroxy, methoxy and ethoxy; (iii) phenyl, or phenyl substituted by methyl, ethyl and alkoxy; or (iv) —(CH$_2$)$_n$Ar, wherein n equals 1 to 4 and Ar is phenyl or substituted phenyl as defined in (iii), which comprises:

reacting a methanesulfonic acid derivative, with a salt, with an organic base, of a compound of Formula II:

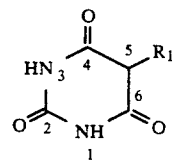

wherein $R_1$ is defined above, thereby producing a mesylate derivative of Formula III:

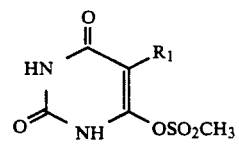

wherein $R^1$ is as defined above; and then
reducing the compound of Formula III with a reducing agent or with molecular hydrogen in the presence of a transition metal to give the desired compound of Formula I.

2. The process of claim 1, wherein up to three moles of said methanesulfonic acid derivative are reacted per mole of organic or inorganic salt of the compound of Formula II in an organic solvent at a temperature ranging from −40° C. to 60° C. for a period of from 10 minutes to 1 day.

3. The process of claim 2, wherein said organic solvent is dimethylformamide, tetrahydrofurane, dimethylsulfoxide, methylene chloride, acetonitrile or acetone.

4. The process of claim 1, wherein the reduction of the compound of Formula III is conducted in a solvent in the presence of a catalyst and of molecular hydrogen or another reducing agent at a temperature of from −20° C. to 60° C. for a period of from 10 minutes to 10 hours.

5. The process of claim 4, wherein the solvent is an alcohol, water, acetic acid or a mixture of two or more of these materials, and said transition metal catalyst is Pd/C, Pd/CaCO$_3$, Pd/BaSO$_4$ or Pt.

6. A process according to claim 1 in which $R_1$ represents hydrogen or fluorine atom, or a $C_1$ or $C_2$ alkyl group unsubstituted or substituted by one or more halogen atom, or a said —(CH$_2$)$_n$Ar group wherein n is 1 or 2.

* * * * *

UNITED STATES PATENT AND TRADEMARK OFFICE
CERTIFICATE OF CORRECTION

PATENT NO. : 5,286,861
DATED      : February 15, 1994
INVENTOR(S): Angelo Bedeschi et al.

It is certified that error appears in the above-indentified patent and that said Letters Patent is hereby corrected as shown below:

On the title page, Item [21],

The Application number should read: --920,507--

Signed and Sealed this

Fourteenth Day of June, 1994

Attest:

BRUCE LEHMAN

Attesting Officer

Commissioner of Patents and Trademarks